US005691191A

United States Patent [19]

Heins et al.

[11] Patent Number: 5,691,191
[45] Date of Patent: Nov. 25, 1997

[54] MEDIUM FOR THE CULTIVATION OF LAGENIDIUM GIGANTEUM

[75] Inventors: Sherry Darlene Heins, Davis; Duane Douglas Ewing, Woodland; Pamela Gail Marrone, Davis, all of Calif.

[73] Assignee: AgraQuest, Inc., Davis, Calif.

[21] Appl. No.: 616,738

[22] Filed: Mar. 15, 1996

[51] Int. Cl.[6] .......... C12N 1/14
[52] U.S. Cl. .......... 435/256.8; 435/244; 435/254.1
[58] Field of Search .......... 435/256.8, 244, 435/254.1

[56] References Cited

U.S. PATENT DOCUMENTS 4,687,744 8/1987 Kerwin et al. .......... 435/242
5,360,607 11/1994 Eyal et al. .......... 424/93.5

OTHER PUBLICATIONS

Kerwin JL et al., J. Am. Mosquito Control Assoc. 10(3) : 451–455 (1994).
Kerwin JL et al., Can. J. Microbiol. 32 : 294–300 (1986).
Kerwin JL et al., J. Invetebr. Pathol. 47(3) : 258–70 (1986).
Kerwin JL et al., J. Invetebr. Pathol. 58(3) : 408–14 (1991).
Kerwin et al., "Ground and aerial application of the sexual and asexual stages of *Lagenidium giganteum* (Oomycetes: Lagenidiales) for mosquito control" *J. Am. Mos. Control Assoc.* (1986) 2(2):182–189.
Kerwin et al., "Field evaluation of *Lagenidium giganteum* (Oömycetes: Lagenidiales) and description of a natural epizoötic involving a new isolate of the fungus" *J. Med. Entomol.* (1988) 25(6):452–460.
Lord et al., "The effects of culture medium quality and host passage on zooporogenesis, oosporogenesis and infectivity of *Langenidium giganteum* (Oomycetes: Lagenidiales)" *J. Invertebr. Pathol.* (1986) 48:355–361.

*Primary Examiner*—Sandra E. Saucier
*Attorney, Agent, or Firm*—Morrison & Foerster

[57] ABSTRACT

A nutrient medium used in fermentation for increasing the yield of cells or microorganisms is provided. The formulation provided increases the yield of the fungus *Lagenidium giganteum* two- to three-fold over known media. The medium contains peptone, yeast extract, Proflo® cottonseed flour, glucose, palm oil, cholesterol, $CaCl_2$ and $MgCl_2$.

4 Claims, No Drawings

MEDIUM FOR THE CULTIVATION OF LAGENIDIUM GIGANTEUM

FIELD OF THE INVENTION

This invention relates to a novel medium for use in fermentation which provides an increased cell yield compared to that of known media. More particularly, the present invention produces at least a two to three-fold increase in the yield of the fungus *Lagenidium giganteum* compared to the yield obtained with known media. In addition to increasing yield of cells, *L. giganteum* grown in novel medium containing lecithin exhibits increased effectiveness against mosquitoes.

BACKGROUND OF THE INVENTION

Fermentation is the process of growing microorganisms or cells in specialized vessels. The cells or organisms may then be purified and used for a variety of purposes. For instance, the fungus *Lagenidium giganteum* grown in fermenters is used as a biocontrol agent for mosquitoes.

Optimal growth of the microorganism during fermentation depends on several factors including available nutrients, oxygen concentration, pH, temperature, and degree of mixing. Nutrients necessary for cell growth are provided in the medium used during the fermentation process. Accordingly, the yield obtained from fermentation depends, in part, on the composition of the medium.

There are several published nutrient media currently used in the fermentation of *Lagenidium giganteum*. All use deionized water added to a final volume of 1L, and all are sterilized. One formulation comprises 2.0 g Ardamine pH, 2.0 g glucose, 1 mL corn oil, 0.5 g cholesterol and 2 mM Ca2+. (Kerwin, James L. and Washino, Robert K. (1986) "Ground and aerial application of the sexual and asexual stages of *Lagenidium giganteum* (oomycetes: Lagenidiales) for mosquito control." *J. Am. Mos. Control Assoc.* 2 (2): 182–189).

Another formulation comprises 2.0 g autolyzed yeast extract, 1.0 g proflo, 0.5 g fish meal, 2 mM —$CaCl_2 \cdot 2H_2O$, 1 mM $MgCl_2 \cdot 6H_2O$, 0.05 g cholesterol and 2 mL cottonseed oil. (Kerwin, James L. and Washino, Robert K. (1988) "Field evaluation of *Lagenidium giganteum* (Oomycetes: Lagenidiales) and description of a natural epizootic involving a new isolate of fungus." *J. Meal EntomoL.* 25 (6): 452–460) Yet another fermentation medium comprises 1.25 g glucose, 1.25 g peptone, 1.25 g autolyzed yeast extract, 2 g corn oil, 1 g linseed oil, and 0.075 g $CaCl_2 \cdot 2H_2O$ (U.S. Pat. No. 4,687,744). The fourth published medium contains 1.25 g yeast extract, 1.2 g glucose, 3.2 g powdered wheat germ, hemp seed extract to provide 250 mg/L of soluble protein, 1.25 g bactopeptone, 3 g glucose and 1.5 g corn oil. (Lord, Jeffrey C. and Roberts, Donald W. (1986) "The effects of culture medium quality and host passage on zoosporogensis and infectivity of *Lagenidium giganteum* (Oomycetes: Lagenidiales)," *J. Invertebr. Pathol.* 48:355–361)

When used in fermentation, the above-referenced published medium formulations all yield approximately the same number of cells and infect susceptible mosquitoes at approximately the same rate. Thus, in order to increase the yield and infectivity of biocontrol agents like *Lagenidium giganteum*, there is a need for an improved fermentation medium.

SUMMARY OF THE INVENTION

A medium for use in fermentation consisting essentially of 3.6 g per liter peptone; 3.0 g per liter autolyzed yeast extract; 3.6 g per liter peptone; 1.5 to 3.0 g per liter autolyzed yeast extract; 1.6 g per liter Proflo® cottonseed flour (Traders Protein, Memphis, Tenn.), which is approximately 58% protein (dry weight); 2.0 to 7.75 g per liter glucose (dextrose); 2.5 g per liter palm oil; 0.2 g per liter cholesterol; 0.6 g per liter $CaCl_2 \cdot 2H_2O$; 0.2 g per liter $MgCl_2 \cdot 6H_2O$ and, optionally, 0.0 to 2.0 g per liter of lecithin. This medium provides increased yields of *Lagenidium giganteum* compared to prior art media, and, yield and infectivity of the organism is further increased when lecithin is included in the medium.

DESCRIPTION OF THE PREFERRED EMBODIMENTS

The present invention relates to an improved medium for fermentation. The medium increases yield at least approximately two to three fold over known media. The invention is useful in large scale production of *Lagenidium giganteum*, a biocontrol agent for mosquitoes.

Definitions

As used herein, the term "fermentation" refers to the process of growing cells or microorganisms in specialized vessels. "Nutrient medium" ("medium") refers to a solid or liquid substrate that will support the growth of an organism.

In a preferred embodiment of this invention, the nutrient medium is prepared as follows:

3.6 g per liter peptone;
1.5 to 3 g per liter autolyzed yeast extract;
1.6 g per liter Proflo® cottonseed flour (Traders Protein, Memphis, Tenn.), which is approximately 58% protein (dry weight);
2.0 to 7.75 g per liter glucose (dextrose);
2.5 g per liter palm oil;
0.2 g per liter cholesterol;
0.6 g per liter $CaCl_2 2H_2O$; and
0.2 g per liter $MgCl_2 6H_2O$.

Deionized water is added to a final volume of 1L and the pH is adjusted to 6.5. The constituents are heated until dissolved and then the medium is sterilized by autoclaving at 121° C., 15 p.s.i., for 30 minutes. When used in the fermentation of *Lagenidium giganteum*, this medium increases yield at least two to three fold over known media.

In another preferred embodiment, the nutrient medium is prepared by adding up to 2.0 g per liter of lecithin to the above formulation.

The following example is provided only for illustrative purposes, and is not to be construed as limiting the invention in any way.

EXAMPLE 1

Shake flask comparison of growth rates of *Lagenidium giganteum* in different media Growth rate in the novel nutrient medium was compared with two other media in side by side shake flask experiments.

Medium #1:
 1.25 g glucose (dextrose)
 1.25 g peptone
 1.25 g autolyzed yeast extract
 2.0 g corn oil
 1.0 g palm oil
 0.03 g cholesterol
 0.4 g $CaCl_2 2H_2O$
 0.2 g $MgCl_2 6H_2O$
Medium #2:
 1.2 g peptone 1.2 g autolyzed yeast extract
3.0 g glucose (dextrose)
0.5 g cholesterol Novel Nutrient Medium:
  3.6 g peptone
  3.0 g autolyzed yeast extract
  1.6 g Proflo® cottonseed flour (Traders Protein, Memphis, Tenn.), which is approximately 58% protein (dry weight) extract
  2.0 g glucose (dextrose)
  2.5 g palm oil
  0.2 g cholesterol
  0.6 g $CaCl_2 2H_2O$
  0.2 g $MgCl_2 6H_2O$ When preparing each of the media, all ingredients were combined and deionized water was added to a final volume of 1L. The pH was adjusted to 6.5. Contents were heated in a microwave until dissolved and then sterilized at 121° C., 15 psi for 30 minutes. For each medium, nine 250 mL flasks were each filled with 50 mL of medium. A disk of *Lagenidium giganteum* (California strain) taken from a petri dish was used to inoculate each flask. The flasks were shaken at 120 rpm, 29° C. in an orbital temperature controlled shaker for 7 days. Cells were harvested by centrifuging the fungal mass at 5,200 rpm for 20 minutes at 18° C. The centrifuged cell mass was weighed and cell counts made with a hemacytometer. Mean cell counts were recorded. Results are summarized in Table 1.

TABLE 1

|  | Medium #1 | Medium #2 | Novel Nutrient Medium | Fold Increase in cells/mL when Novel Medium used |
|---|---|---|---|---|
| Exp't #1 | $1.2-2.0 \times 10^6$ cells/mL | $1.2-2.0 \times 10^6$ cells/mL | $4.4 \times 10^6$ cells/mL | 2.2 fold |
| Exp't #2 | $6.25 \times 10^5$ cells/mL | $7.5 \times 10^5$ cells/mL | $1.38 \times 10^6$ cells/mL | 1.84–2.2 fold |
| Exp't #3 | $2.97 \times 10^5$ cells/mL | $3.3 \times 10^5$ cells/mL | $4.75 \times 10^5$ cells/mL | 1.4–1.6 fold |
| Bxp't #7 | $9.77 \times 10^4$ cells/mL | not done | $9.38 \times 10^5$ cells/mL | 9.6 fold |
| Exp't #8 | $1.93 \times 10^5$ cells/mL | not done | $7.30 \times 10^5$ cells/mL | 3.7 fold |

Medium #1 and Medium #2 yielded approximately the same number of cells per mL of medium in each experiment. The novel nutrient medium consistently increased the number of cells/mL in comparison to either Medium #1 or Medium #2. The average yield of *Lagenidium giganteum* was increased approximately three and half fold when grown in the novel nutrient medium.

EXAMPLE 2

Shake flask comparison of novel medium with lecithin added

Having established that the novel medium formulation of Example 1 increases cell yield over known media, the effect of varying amounts of dextrose and yeast extract and adding 1.0 g or 2.0 g lecithin to the basal novel medium was examined. All media were homogenized with a large probe at 70% speed for 10–15 seconds to ensure components were in solution. Using EmReagents color Phast®, the pH of all media was adjusted to 6.5 and sterilized as in Example 1. For each medium, three 250 mL flasks were filled with 50 mL of medium, inoculated, cultured and harvested as described in Example 1. Results are summarized in Table 2 and Table 3

TABLE 2

| Dextrose % Wt | Yeast extract % Wt | Lecithin % Wt | Cell Yield (cells/mL) | |
|---|---|---|---|---|
| 0.8750 | 0.1250 | 0.0000 | $2.0 \times 10^5$ | Average Cell |
| 0.8750 | 0.1250 | 0.0000 | $3.0 \times 10^5$ | Yield (cells/mL) |
| 0.6875 | 0.3125 | 0.0000 | $4.8 \times 10^5$ | without lecithin: |
| 0.5000 | 0.5000 | 0.0000 | $4.1 \times 10^5$ | $3.6 \times 10^5$ |
| 0.5000 | 0.5000 | 0.0000 | $4.13 \times 10^5$ | |
| 0.5875 | 0.3125 | 0.1000 | $5.4 \times 10^5$ | Average Cell |
| 0.5875 | 0.3125 | 0.1000 | $4.05 \times 10^5$ | Yield (cells/mL) |
| 0.3000 | 0.5000 | 0.2000 | $7.4 \times 10^5$ | with lecithin: |
| 0.3000 | 0.5000 | 0.2000 | $4.9 \times 10^5$ | $4.63 \times 10^5$ |
| 0.6750 | 0.1250 | 0.2000 | $4.5 \times 10^5$ | |
| 0.6750 | 0.1250 | 0.2000 | $4.1 \times 10^5$ | |
| 0.4875 | 0.3125 | 0.2000 | $3.6 \times 10^5$ | |

As shown in Table 2, for media without lecithin, the average cells/mL yield is $3.6 \times 10^5$. With lecithin, yield increases to $4.63 \times 10^5$ cells/mL.

EXAMPLE 3

Infectivity of *Lagenidium giganteum* grown in various media

*Lagenidium giganteum* was grown in novel media described in Example 2 which contained no lecithin, 0.1000% by weight lecithin or 0.2000 % by weight lecithin. Culturing conditions were as described in Example 1. The concentration of cells was calculated and their ability to kill mosquitoes measured at concentrations of 5,000; 2,500; 1,250 and 675 cells/mL. Results summarized in Table 3 are averages of duplicate experiments.

TABLE 3

|  | % Mortality at 5,000 cells/mL | % Mortality at 2,500 cells/mL | % Mortality at 1,250 cells/mL | % Mortality at 675 cells/mL |
|---|---|---|---|---|
| Medium without lecithin | 66 | 67 | 61 | 51 |
| Medium with lecithin | 87 | 87 | 89 | 74 |

These results illustrate that *Lagenidium giganteum* grown in the novel media killed more mosquitoes than cells grown in media without added lecithin.

We claim:

1. A medium for use in fermentation, consisting essentially of:

(a) 3.6 g per liter peptone;

(b) 1.5 to 3 g per liter autolyzed yeast extract;

(c) 1.6 g per liter Proflo® cottonseed flour;

(d) 2.0 to 7.75 g per liter dextrose;

(e) 2.5 g per liter palm oil;

(f) 0.2 g per liter cholesterol;

(g) 0.6 g per liter $CaCl_2 \cdot 2H_2O$; and (h) 0.2 g per liter $MgCl_2 \cdot 6H_2O$.

2. A medium for use in fermentation, consisting essentially of:

(a) 3.6 g per liter peptone;

(b) 1.5 to 3 g per liter autolyzed yeast extract;

(c) 1.6 g per liter Proflo® cottonseed flour;

(d) 2.0 to 7.75 g per liter dextrose;

(e) 2.5 g per liter palm oil;

(f) 0.2 g per liter cholesterol;

(g) 0.6 g per liter $CaCl_2 \cdot 2H_2O$;

(h) 0.2 g per liter $MgCl_2 \cdot 6H_2O$; and (i) lecithin up to 2.0 g per liter.

3. The medium according to claim 1, for use in culturing *Lagenidium giganteum*.

4. The medium according to claim 2, for use in culturing *Lagenidium giganteum*.

* * * * *